United States Patent [19]

Fukuoka et al.

[11] Patent Number: 5,189,183
[45] Date of Patent: Feb. 23, 1993

[54] AROMATIC AMINE DERIVATIVES

[75] Inventors: Daisuke Fukuoka, Iwakuni; Katsuya Takahashi, Ohtake; Isao Hashimoto, Iwakuni, all of Japan

[73] Assignee: Mitsui Petrochemical Industries, Ltd., Tokyo, Japan

[21] Appl. No.: 598,061

[22] Filed: Oct. 16, 1990

Related U.S. Application Data

[62] Division of Ser. No. 151,594, Feb. 2, 1988, Pat. No. 5,011,950.

[30] Foreign Application Priority Data

Feb. 5, 1987 [JP] Japan .................................. 62-23553

[51] Int. Cl.$^5$ .................. C07D 307/04; C07D 311/90
[52] U.S. Cl. ...................................... 549/345; 549/386; 549/387; 549/395; 549/399; 549/400; 549/401; 549/408
[58] Field of Search ............... 549/336, 386, 387, 400, 549/434, 437, 445, 458, 462, 466, 345, 395, 399, 401, 408

[56] References Cited

U.S. PATENT DOCUMENTS

| | | | |
|---|---|---|---|
| 4,426,385 | 1/1984 | Cain | 546/269 |
| 4,838,924 | 6/1989 | Takematsa et al. | 549/386 |
| 5,011,950 | 4/1991 | Fukuoka et al. | 549/386 |

OTHER PUBLICATIONS

Matsumoto et al., CA 107:1758721.
Takematsu et al., CA 107:236509b.

*Primary Examiner*—C. Warren Ivy
*Assistant Examiner*—Raymond Covington
*Attorney, Agent, or Firm*—Sherman and Shalloway

[57] ABSTRACT

Novel aromatic amine derivatives of specific structure are useful intermediates for herbicides. The aromatic amine compounds have the structure shown by formula [I]:

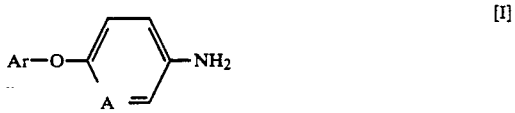

wherein Ar and A are as defined herein.

26 Claims, No Drawings

AROMATIC AMINE DERIVATIVES

This is a division of application Ser. No. 07/151,594, filed Feb. 2, 1988 now U.S. Pat. No. 5,011,950.

BACKGROUND OF THE INVENTION

This invention relates to novel aromatic amine derivatives.

Wheat, corn, rice, and soybean plants are important crops. A variety of herbicides have been applied in order to increase crop yields. Prior art herbicides are not satisfactory in herbicidal activity and safety to growing crops. There is a need for a safe herbicide which can control weeds at a low level of application while giving no or little phytotoxity to growing crops.

During our research to produce a herbicide which is applicable in a small amount to kill weeds without phytotoxity to growing crops, we have discovered novel aromatic amine derivatives which are useful as intermediates for herbicides meeting the above requirements.

SUMMARY OF THE INVENTION

An object of the present invention is to provide novel aromatic amine derivatives which are useful as intermediates for herbicides.

According to the present invention, there is provided a novel aromatic amine derivative of the general formula [I]:

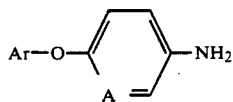

[I]

wherein Ar is a radical selected from the group consisting of

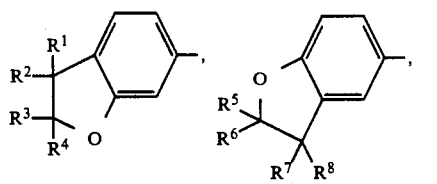

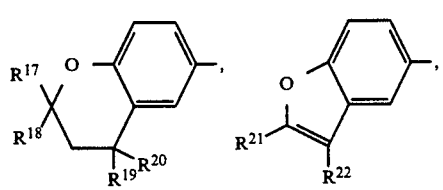

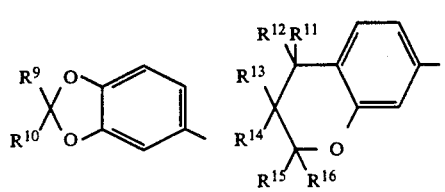

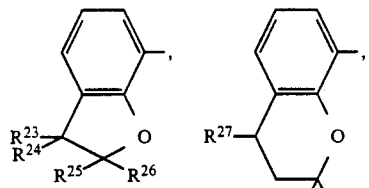

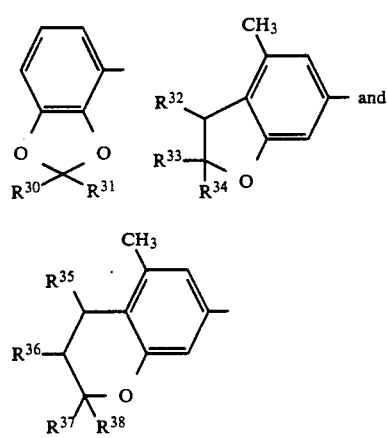

wherein $R^1$ to $R^{15}$ and $R^{17}$ to $R^{38}$ may be the same or different and are independently selected from the group consisting of hydrogen, lower alkyl radicals, and lower alkoxyl radicals, $R^{16}$ is selected from the group consisting of hydrogen, lower alkyl radicals, lower alkoxyl radicals and hydroxyl, with the proviso that $R^2$ and $R^3$, $R^6$ and $R^7$, $R^9$ and $R^{10}$, and $R^{15}$, or $R^{15}$ and $R^{16}$ may, taken together, represent an alkylene chain, which may be substituted with a lower alkyl radical, to form a 5- or 6-membered ring with the carbon atoms to which they are attached, $R^{11}$ and $R^{12}$ may, taken together, represent an ethylene dioxyl radical, or $R^{14}$ and $R^{15}$ may, taken together, represent a dichloromethylene radical; and A is a nitrogen atom or $$-\underset{X}{\overset{}{C}}=$$

wherein X is selected from the group consisting of a hydrogen atom, a chlorine atom, a nitro radical, and a trifluoromethyl radical, when both $R^5$ and $R^6$ are methyl radicals and $$A \text{ is } -\underset{H}{\overset{}{C}}=,$$

at least one of $R^7$ and $R^8$ does not represent hydrogen atom, when both $R^{25}$ and $R^{26}$ are methyl radicals and $$A \text{ is } -\underset{H}{\overset{}{C}}=,$$

at least one of $R^{23}$ and $R^{24}$ does not represent hydrogen atom.

DETAILED DESCRIPTION OF THE INVENTION

The aromatic amine derivatives of the present invention have the general formula [I] as defined above.

Examples of the lower alkyl radicals represented by $R^1$ through $R^{38}$ include methyl, ethyl, n-propyl, isopropyl, n-butyl, isobutyl, sec-butyl, tert-butyl, etc. Examples of the lower alkoxyl radicals represented by $R^1$ through $R^{38}$ include methoxy, ethoxy, n-propoxy, isopropoxy, n-butoxy, isobutoxy, sec-butoxy, etc.

Examples of the radicals represented by Ar are shown below.

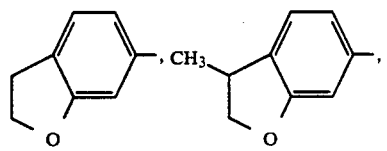
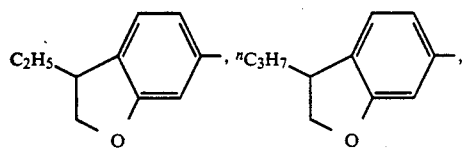
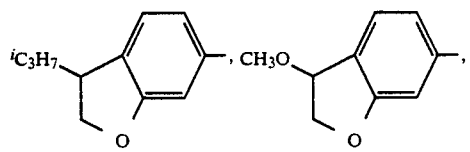
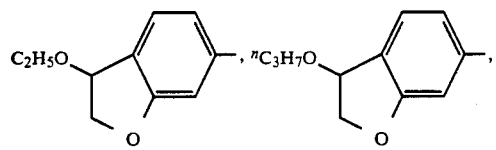
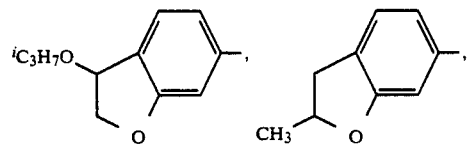
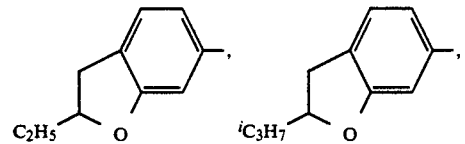
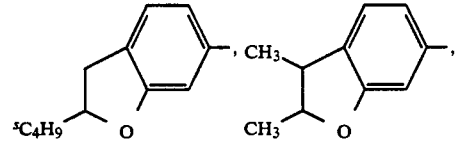
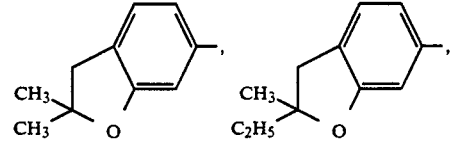

-continued

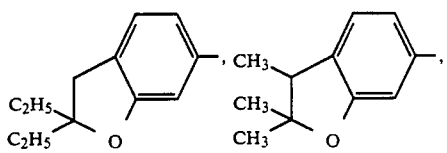
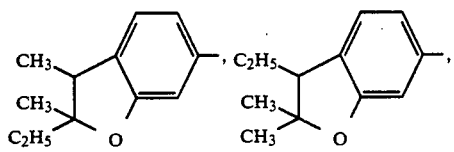
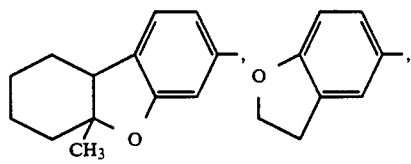
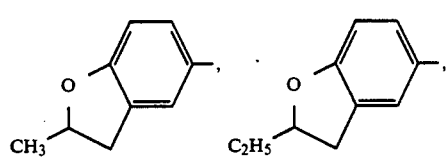
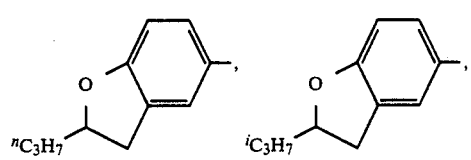
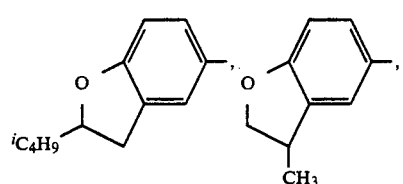
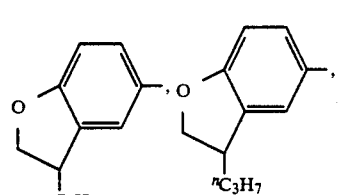
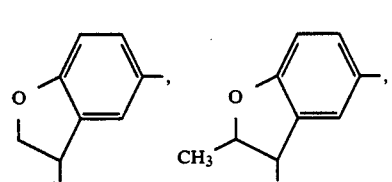
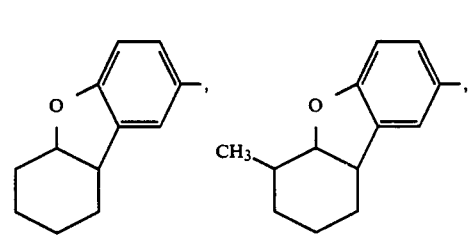

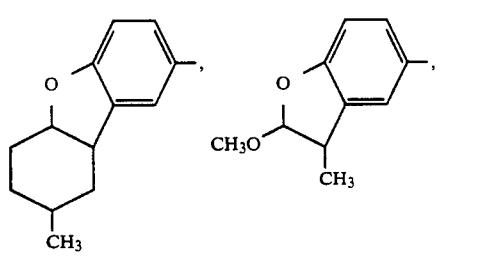
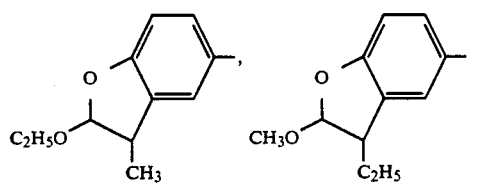
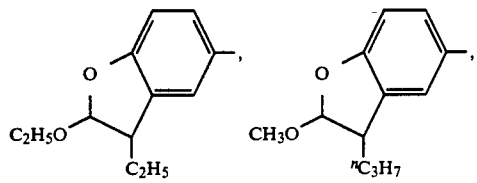
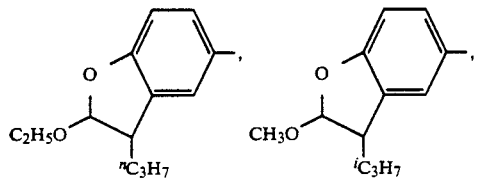
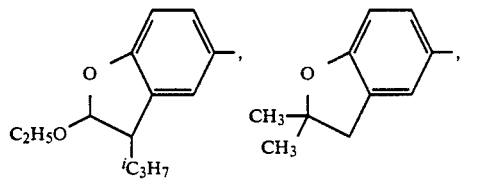
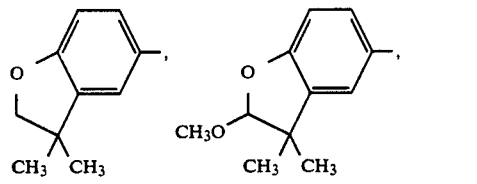
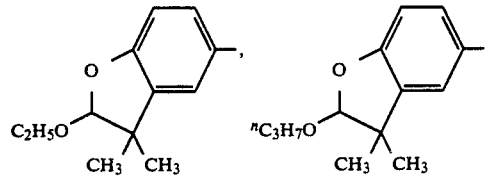
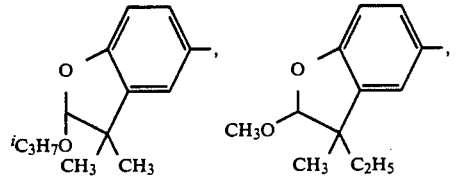
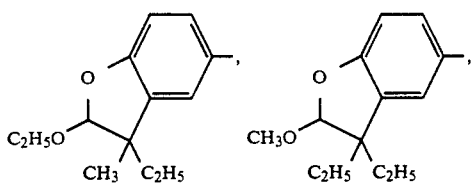
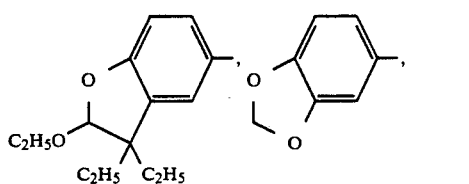
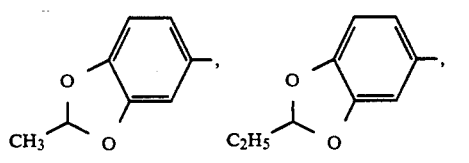
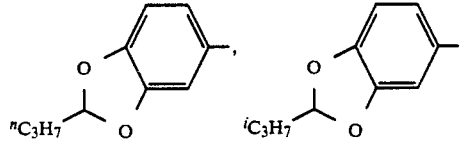
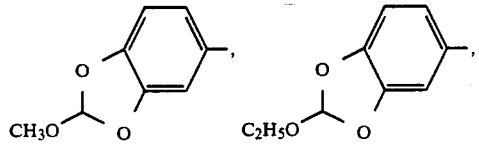
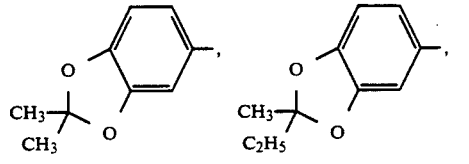
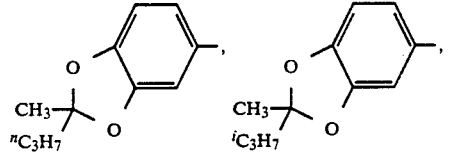
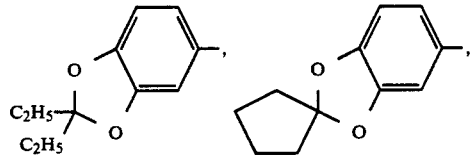
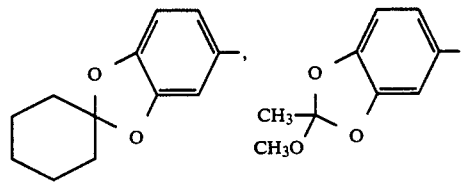

-continued
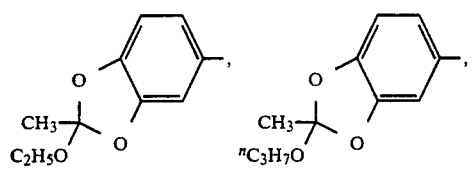
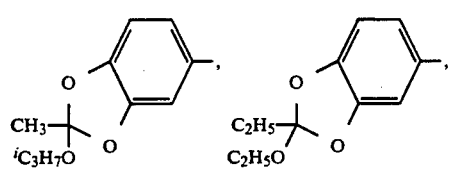
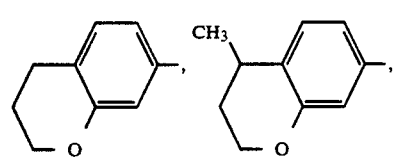
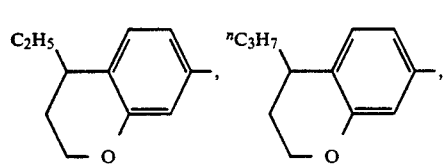
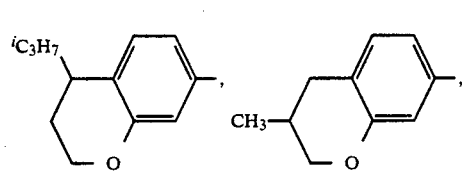
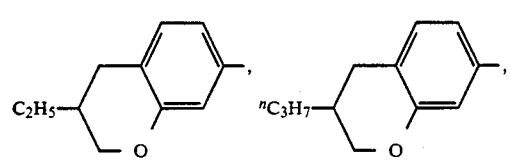
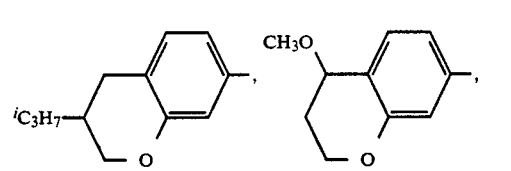
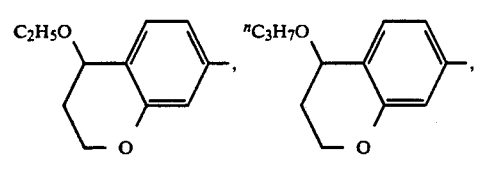
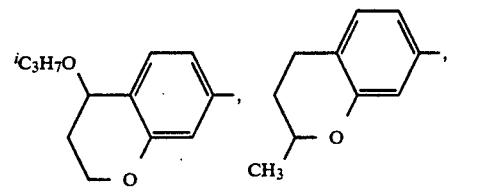
-continued
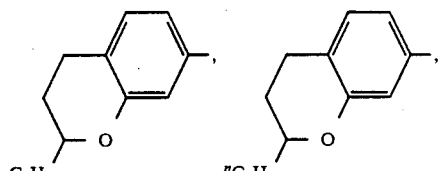
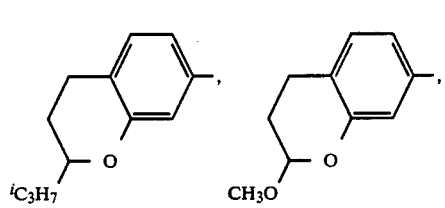
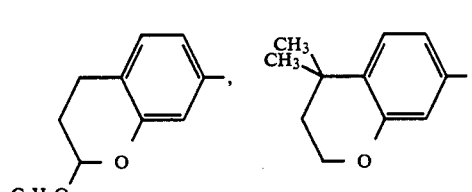
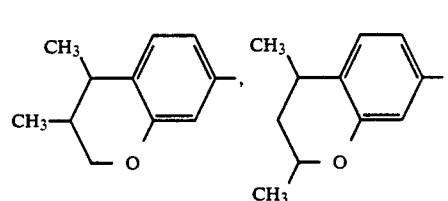
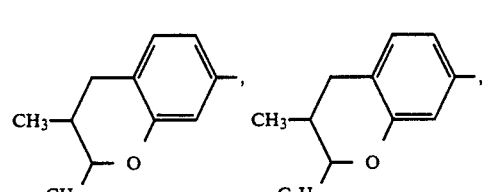
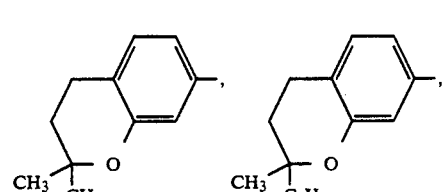
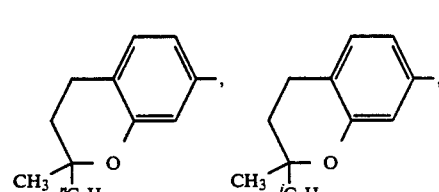
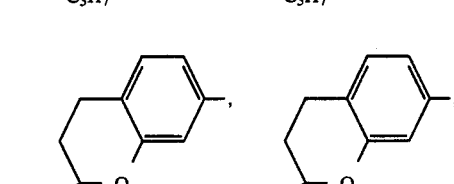

-continued
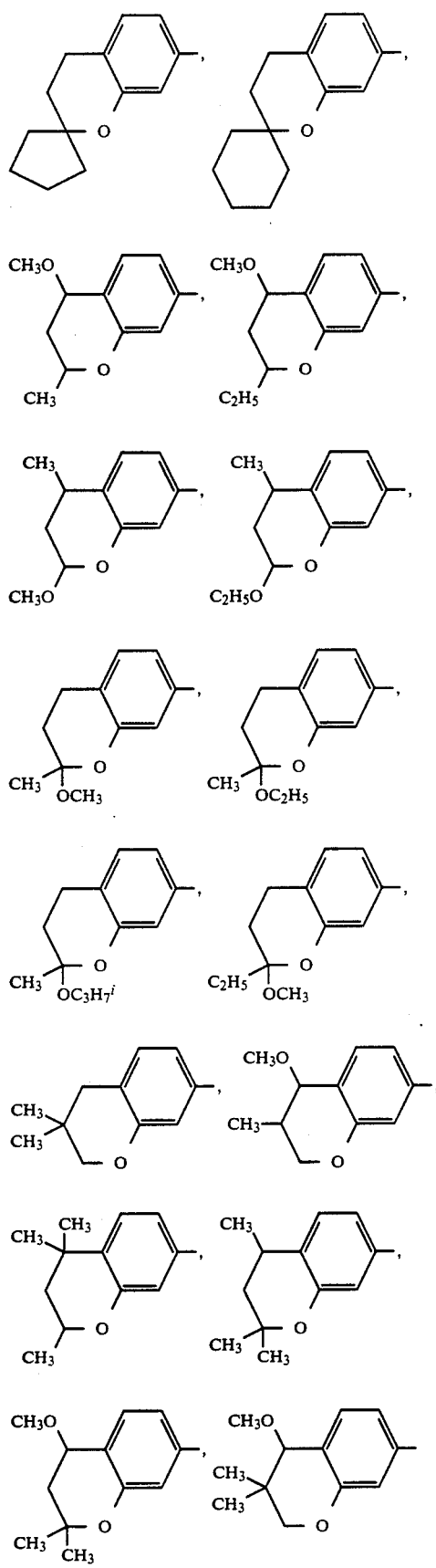
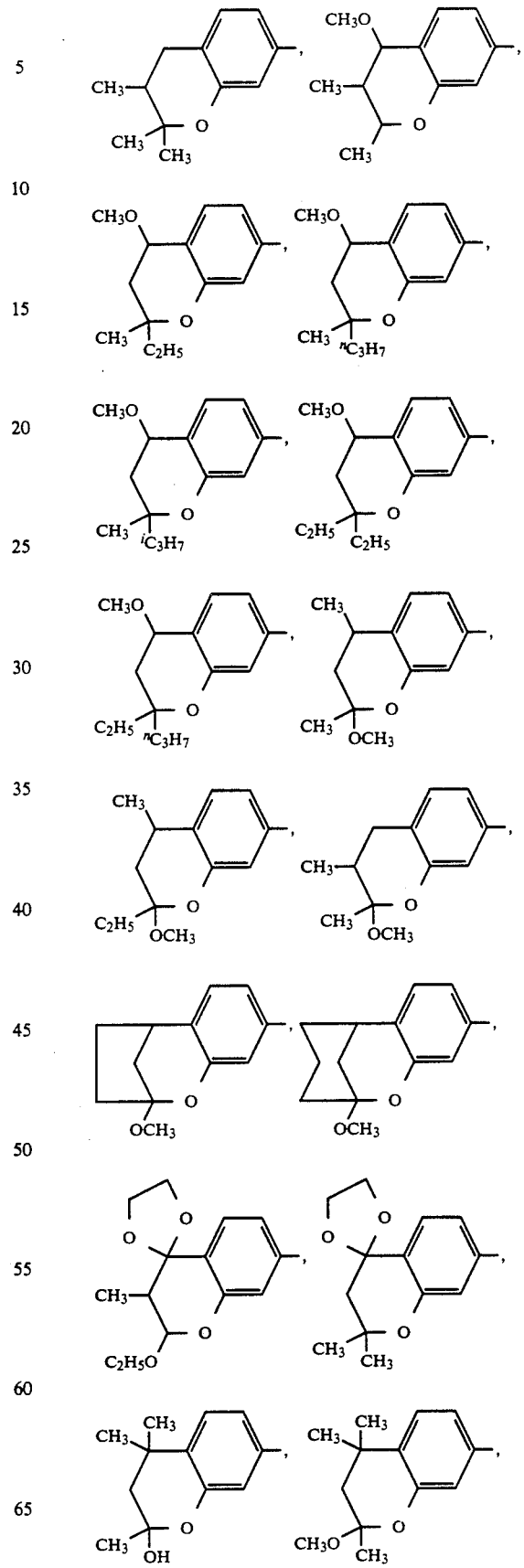

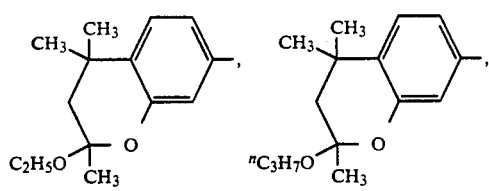
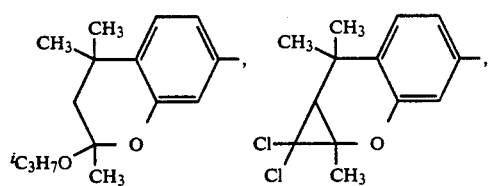
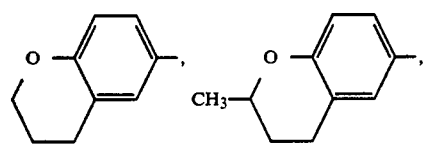
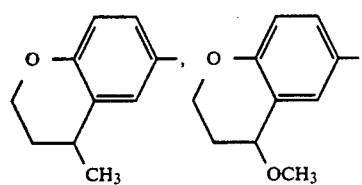
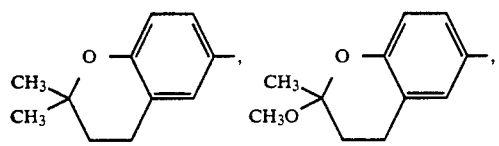
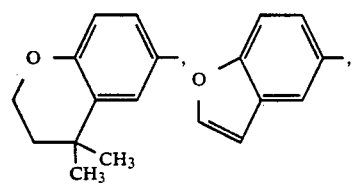
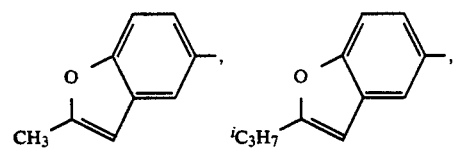
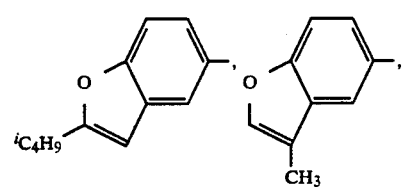
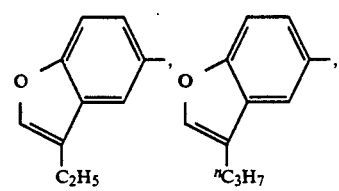
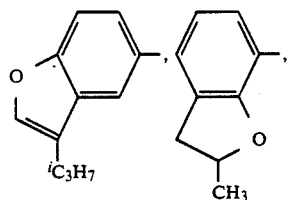
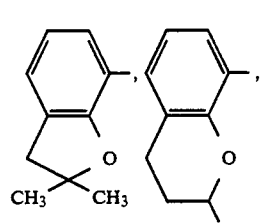
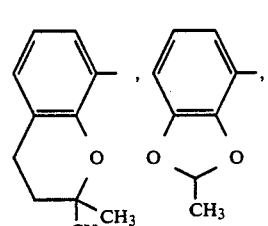
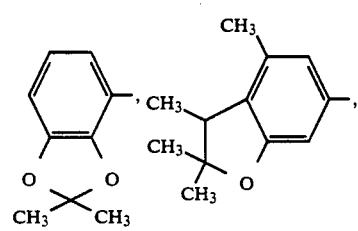
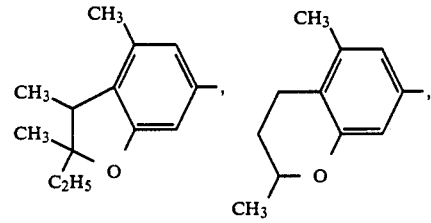
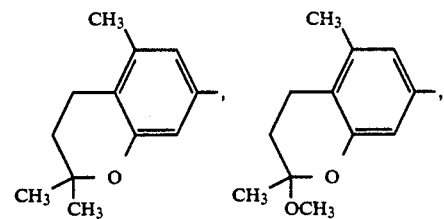
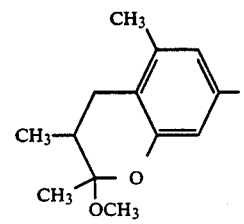
Preferred examples of the aromatic amine derivatives of the present invention are shown in Tables 1 through 11. Particularly preferred examples of the aromatic amine derivatives of the present invention are compounds shown in Tables 1, 3, 4, 5, 6, 8, 9, 10 and 11.

TABLE 1

| Compound No. | $R^1$ | $R^2$ | $R^3$ | $R^4$ | A |
|---|---|---|---|---|---|
| 1 | $CH_3$ | H | H | H | pyridine-2,5-diyl |
| 2 | $CH_3$ | H | H | H | 1,4-phenylene |
| 3 | $CH_3$ | H | $CH_3$ | $CH_3$ | pyridine-2,5-diyl |
| 4 | $CH_3$ | H | $CH_3$ | $CH_3$ | 1,4-phenylene |
| 5 | H | H | H | H | 1,4-phenylene |
| 6 | $C_2H_5$ | H | H | H | 1,4-phenylene |
| 7 | $C_3H_7{}^n$ | H | H | H | 1,4-phenylene |
| 8 | $CH_3$ | H | $CH_3$ | H | 1,4-phenylene |
| 9 | H | H | $CH_3$ | H | 1,4-phenylene |
| 10 | H | H | $C_2H_5$ | H | 1,4-phenylene |

TABLE 1-continued

| Compound No. | $R^1$ | $R^2$ | $R^3$ | $R^4$ | A |
|---|---|---|---|---|---|
| 11 | H | H | $C_3H_7{}^i$ | H | 1,4-phenylene |
| 12 | H | H | $C_4H_9{}^s$ | H | 1,4-phenylene |
| 13 | H | H | $CH_3$ | $CH_3$ | 1,4-phenylene |
| 14 | H | H | $CH_3$ | $C_2H_5$ | 1,4-phenylene |
| 15 | H | H | $C_2H_5$ | $C_2H_5$ | 1,4-phenylene |
| 16 | $CH_3$ | H | $CH_3$ | $C_2H_5$ | pyridine-2,5-diyl |
| 17 | $CH_3$ | H | $CH_3$ | $C_2H_5$ | 1,4-phenylene |
| 18 | $CH_3$ | H | $CH_3$ | $C_2H_5$ | 3-Cl-1,4-phenylene |
| 19 | $CH_3$ | H | $CH_3$ | $C_2H_5$ | 3-NO$_2$-1,4-phenylene |
| 20 | $CH_3$ | H | $CH_3$ | $C_2H_5$ | 3-CF$_3$-1,4-phenylene |

TABLE 1-continued

[Structure: phenyl ring with R¹, R², R³, R⁴ substituents on a fused dihydrofuran ring (with O), connected via ether O to another aromatic ring A bearing NH₂]

| Compound No. | R¹ | R² | R³ | R⁴ | A |
|---|---|---|---|---|---|
| 21 | $C_2H_5$ | H | $CH_3$ | $CH_3$ | para-phenylene |
| 22 | H | —$(CH_2)_4$— | | $CH_3$ | para-phenylene |

TABLE 2

[Structure: phenyl ring with fused dihydrofuran bearing R⁵, R⁶, R⁷, R⁸, connected via ether O to aromatic ring A bearing NH₂]

| Compound No. | R⁵ | R⁶ | R⁷ | R⁸ | A |
|---|---|---|---|---|---|
| 23 | $CH_3$ | H | H | H | pyridine |
| 24 | $CH_3$ | H | H | H | para-phenylene |
| 25 | H | H | $CH_3$ | H | para-phenylene |
| 26 | H | H | $C_2H_5$ | H | para-phenylene |
| 27 | H | H | $C_3H_7{}^n$ | H | para-phenylene |
| 28 | H | H | $C_3H_7{}^i$ | H | para-phenylene |
| 29 | $C_3H_7{}^i$ | H | H | H | para-phenylene |
| 30 | $OCH_3$ | H | $C_2H_5$ | H | para-phenylene |
| 31 | $CH_3$ | H | $CH_3$ | H | pyridine |
| 32 | $CH_3$ | H | $CH_3$ | H | para-phenylene |
| 33 | $CH_3$ | $CH_3$ | H | H | pyridine |
| 35 | H | H | $CH_3$ | $CH_3$ | para-phenylene |
| 36 | $OC_2H_5$ | H | $CH_3$ | H | para-phenylene |
| 37 | $OCH_3$ | H | $CH_3$ | $CH_3$ | pyridine |
| 38 | $OCH_3$ | H | $CH_3$ | $CH_3$ | para-phenylene |
| 39 | $OCH_3$ | H | $CH_3$ | $CH_3$ | chlorophenylene |

TABLE 2-continued

Structure: benzene ring with O (bearing R⁵, R⁶, R⁷, R⁸ substituents), connected via O to ring A, which connects to NH₂.

| Compound No. | R⁵ | R⁶ | R⁷ | R⁸ | A |
|---|---|---|---|---|---|
| 40 | OCH₃ | H | CH₃ | C₂H₅ | 1,4-phenylene |
| 41 | OCH₃ | H | C₂H₅ | C₂H₅ | 1,4-phenylene |
| 42 | OCH₃ | H | $C_3H_7^i$ | H | 1,4-phenylene |
| 43 | OC₂H₅ | H | C₂H₅ | H | 1,4-phenylene |
| 44 | OC₂H₅ | H | $C_3H_7^i$ | H | 1,4-phenylene |
| 45 | OC₂H₅ | H | CH₃ | CH₃ | 1,4-phenylene |
| 46 | $OC_3H_7^i$ | H | CH₃ | CH₃ | 1,4-phenylene |
| 47 | H | —(CH₂)₄— | | H | 1,4-phenylene |
| 48 | H | —CH(CH₃)—(CH₂)₃— | | H | 1,4-phenylene |
| 49 | H | —(CH₂)₂—CH(CH₃)—CH₂— | | H | 1,4-phenylene |

TABLE 3

Structure: benzene ring fused to dioxole bearing R⁹, R¹⁰; connected via O to ring A, which connects to NH₂.

| Compound No. | R⁹ | R¹⁰ | A |
|---|---|---|---|
| 50 | H | H | 1,4-phenylene |
| 51 | C₂H₅ | CH₃ | 1,4-phenylene |
| 52 | CH₃ | CH₃ | pyridine (2,5) |
| 53 | CH₃ | CH₃ | 1,4-phenylene |
| 54 | OCH₃ | CH₃ | 1,4-phenylene |
| 55 | OC₂H₅ | CH₃ | 1,4-phenylene |
| 56 | OC₂H₅ | C₂H₅ | 1,4-phenylene |
| 57 | OCH₃ | H | 1,4-phenylene |
| 58 | OC₂H₅ | H | 1,4-phenylene |
| 59 | CH₃ | $C_3H_7^i$ | 1,4-phenylene |
| 60 | C₂H₅ | C₂H₅ | 1,4-phenylene |

TABLE 3-continued
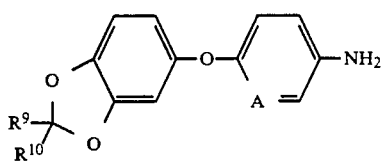
| Compound No. | R⁹ | R¹⁰ | A |
|---|---|---|---|
| 61 | —(CH₂)₄— | | 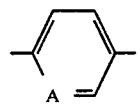 |
TABLE 4
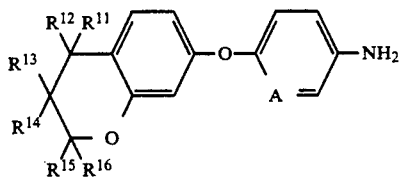
| Compound No. | R¹¹ | R¹² | R¹³ | R¹⁴ | R¹⁵ | R¹⁶ | A |
|---|---|---|---|---|---|---|---|
| 62 | H | H | H | H | H | H | 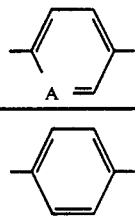 |
| 63 | CH₃ | H | H | H | H | H | 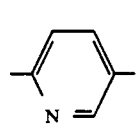 |
| 64 | CH₃ | H | H | H | H | H | 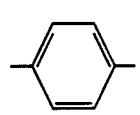 |
| 65 | H | H | H | H | CH₃ | H | 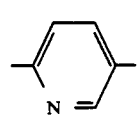 |
| 66 | H | H | H | H | CH₃ | H | 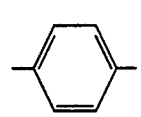 |
| 67 | CH₃ | CH₃ | H | H | H | H | 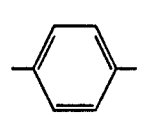 |
| 68 | H | H | H | H | CH₃ | CH₃ | 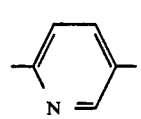 |
| 69 | H | H | H | H | CH₃ | CH₃ | 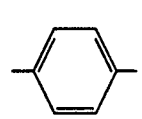 |
| 70 | H | H | H | H | CH₃ | CH₃ | 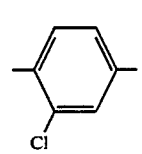 |

TABLE 4-continued
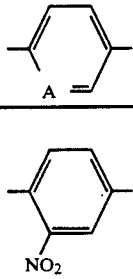
| Compound No. | R11 | R12 | R13 | R14 | R15 | R16 | A |
|---|---|---|---|---|---|---|---|
| 71 | H | H | H | H | CH3 | CH3 | 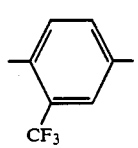 |
| 72 | H | H | H | H | CH3 | CH3 | 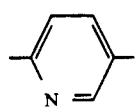 |
| 73 | CH3 | CH3 | H | H | CH3 | H | 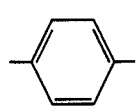 |
| 74 | CH3 | CH3 | H | H | CH3 | H | 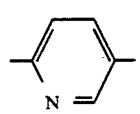 |
| 75 | CH3 | H | H | H | CH3 | CH3 | 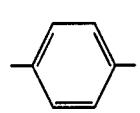 |
| 76 | CH3 | H | H | H | CH3 | CH3 | 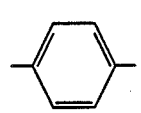 |
| 77 | OCH3 | H | H | H | CH3 | CH3 | 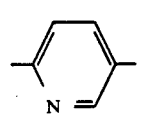 |
| 78 | CH3 | CH3 | H | H | CH3 | OCH3 | 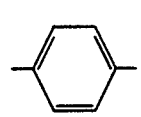 |
| 79 | CH3 | CH3 | H | H | CH3 | OCH3 | |
| 80 | CH3 | CH3 | H | H | CH3 | OCH3 | 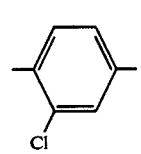 |

TABLE 4-continued
| Compound No. | R11 | R12 | R13 | R14 | R15 | R16 | A |
|---|---|---|---|---|---|---|---|
| 81 | CH3 | CH3 | H | H | CH3 | OCH3 | 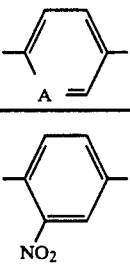 |
| 82 | CH3 | CH3 | H | H | CH3 | OCH3 | 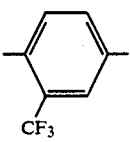 |
| 83 | CH3 | CH3 | H | H | CH3 | OC2H5 | 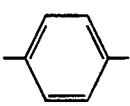 |
| 84 | CH3 | CH3 | H | H | CH3 | OC3H7$^n$ |  |
| 85 | CH3 | CH3 | H | H | CH3 | OC3H7i | 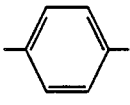 |
| 86 | OCH3 | H | H | H | H | H | 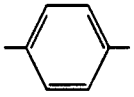 |
| 87 | H | H | H | H | C2H5 | H |  |
| 88 | H | H | H | H | C3H7$^i$ | H | 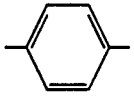 |
| 89 | H | H | H | H | OCH3 | H | 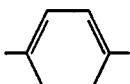 |
| 90 | H | H | H | H | OC2H5 | H | 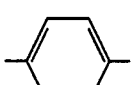 |

TABLE 4-continued

| Compound No. | $R^{11}$ | $R^{12}$ | $R^{13}$ | $R^{14}$ | $R^{15}$ | $R^{16}$ | A |
|---|---|---|---|---|---|---|---|
| 91 | $C_2H_5$ | H | H | H | H | H | p-phenylene |
| 92 | $CH_3$ | H | $CH_3$ | H | H | H | p-phenylene |
| 93 | $CH_3$ | H | H | H | $CH_3$ | H | p-phenylene |
| 94 | $CH_3$ | H | H | H | $OCH_3$ | H | p-phenylene |
| 95 | $CH_3$ | H | H | H | $OC_2H_5$ | H | p-phenylene |
| 96 | $OCH_3$ | H | H | H | $CH_3$ | H | p-phenylene |
| 97 | $OCH_3$ | H | H | H | $C_2H_5$ | H | p-phenylene |
| 98 | H | H | $CH_3$ | H | $CH_3$ | H | p-phenylene |
| 99 | H | H | $CH_3$ | H | $C_2H_5$ | H | p-phenylene |
| 100 | H | H | H | H | $CH_3$ | $C_2H_5$ | p-phenylene |
| 101 | H | H | H | H | $CH_3$ | $C_3H_7^n$ | p-phenylene |

TABLE 4-continued

[Structure: substituted phenyl ether with R11, R12, R13, R14, R15, R16 substituents and A ring connecting to NH2]

| Compound No. | R11 | R12 | R13 | R14 | R15 | R16 | A |
|---|---|---|---|---|---|---|---|
| 102 | H | H | H | H | CH$_3$ | C$_3$H$_7^i$ | para-phenylene |
| 103 | H | H | H | H | C$_2$H$_5$ | C$_2$H$_5$ | para-phenylene |
| 104 | H | H | H | H | C$_2$H$_5$ | C$_3$H$_7^n$ | para-phenylene |
| 105 | H | H | H | H | —(CH$_2$)$_5$— | | para-phenylene |
| 106 | H | H | H | H | CH$_3$ | OCH$_3$ | para-phenylene |
| 107 | H | H | H | H | CH$_3$ | OC$_2$H$_5$ | para-phenylene |
| 108 | H | H | H | H | CH$_3$ | OC$_3$H$_7^i$ | para-phenylene |
| 109 | H | H | H | H | C$_2$H$_5$ | OCH$_3$ | para-phenylene |
| 110 | CH$_3$ | H | H | H | CH$_3$ | OCH$_3$ | para-phenylene |
| 111 | CH$_3$ | H | H | H | C$_2$H$_5$ | OCH$_3$ | para-phenylene |
| 112 | OCH$_3$ | H | CH$_3$ | H | CH$_3$ | H | para-phenylene |

TABLE 4-continued

| Compound No. | R11 | R12 | R13 | R14 | R15 | R16 | A |
|---|---|---|---|---|---|---|---|
| 113 | H | H | CH₃ | H | CH₃ | CH₃ | (1,4-phenylene) |
| 114 | H | H | CH₃ | H | CH₃ | OCH₃ | (1,4-phenylene) |
| 115 | OCH₃ | H | H | H | CH₃ | C₂H₅ | (1,4-phenylene) |
| 116 | OCH₃ | H | H | H | CH₃ | C₃H₇ⁱ | (1,4-phenylene) |
| 117 | OCH₃ | H | H | H | C₂H₅ | C₂H₅ | (1,4-phenylene) |
| 118 | OCH₃ | H | H | H | C₂H₅ | C₃H₇ⁿ | (1,4-phenylene) |
| 119 | —O(CH₂)₂O— | | H | H | CH₃ | H | (1,4-phenylene) |
| 120 | —O(CH₂)₂O— | | H | H | C₂H₅ | H | (1,4-phenylene) |
| 121 | —O(CH₂)₂O— | | H | H | C₃H₇ⁱ | H | (1,4-phenylene) |
| 122 | —O(CH₂)₂O— | | CH₃ | H | CH₃ | H | (1,4-phenylene) |
| 123 | —O(CH₂)₂O— | | H | H | CH₃ | CH₃ | (1,4-phenylene) |

TABLE 4-continued

[Structure: benzene ring with R11,R12,R13,R14,R15,R16 substituents and O linkage, connected via -O- to another ring A with -NH2 group]

| Compound No. | R11 | R12 | R13 | R14 | R15 | R16 | A |
|---|---|---|---|---|---|---|---|
| 124 | —O(CH$_2$)$_2$O— | | H | H | CH$_3$ | C$_2$H$_5$ | para-phenylene |
| 125 | —O(CH$_2$)$_2$O) | | H | H | CH$_3$ | C$_3$H$_7^i$ | para-phenylene |
| 126 | —O(CH$_2$)$_2$O— | | H | H | C$_2$H$_5$ | C$_2$H$_5$ | para-phenylene |
| 127 | —O(CH$_2$)$_2$O— | | H | H | C$_2$H$_5$ | C$_3$H$_7^n$ | para-phenylene |
| 128 | CH$_3$ | CH$_3$ | H | —CCl$_2$— | | CH$_3$ | para-phenylene |
| 129 | [cyclic structure with OCH$_3$] | | | | | | para-phenylene |
| 130 | [cyclic structure with OCH$_3$] | | | | | | para-phenylene |
| 131 | CH$_3$ | CH$_3$ | H | H | CH$_3$ | OH | para-phenylene |

TABLE 5

Structure: R17-O-(CH(R18))-C(R19)(R20)- attached to benzene ring with -O-A-NH2

| Compound No. | R17 | R18 | R19 | R20 | A |
|---|---|---|---|---|---|
| 132 | $CH_3$ | H | H | H | pyridine (2,5) |
| 133 | $CH_3$ | H | H | H | phenyl |
| 134 | $CH_3$ | $CH_3$ | H | H | pyridine (2,5) |
| 135 | $CH_3$ | $CH_3$ | H | H | phenyl |
| 136 | H | H | $CH_3$ | $CH_3$ | phenyl |
| 137 | $CH_3$ | $OCH_3$ | H | H | phenyl |

TABLE 6

Structure: benzofuran with R21, R22 substituents, linked -O-A-NH2

| Compound No. | R21 | R22 | A |
|---|---|---|---|
| 138 | $C_3H_7{}^i$ | H | phenyl |
| 139 | $C_4H_9{}^i$ | H | phenyl |

TABLE 6-continued

| Compound No. | R21 | R22 | A |
|---|---|---|---|
| 140 | H | $C_2H_5$ | phenyl |
| 141 | H | $C_3H_7{}^n$ | phenyl |
| 142 | H | $C_3H_7{}^i$ | phenyl |

TABLE 7

Structure: benzene ring with -O-A-NH2 and fused chroman-type ring with R23, R24, R25, R26

| Compound No. | R23 | R24 | R25 | R26 | A |
|---|---|---|---|---|---|
| 143 | H | H | $CH_3$ | H | pyridine (2,5) |
| 144 | H | H | $CH_3$ | H | phenyl |

TABLE 8

Structure: chroman system with R27, R28, R29 and -O-A-NH2

TABLE 8-continued

| Compound No. | $R^{27}$ | $R^{28}$ | $R^{29}$ | A = |
|---|---|---|---|---|
| 146 | H | CH$_3$ | CH$_3$ | |

TABLE 9

| Compound No. | $R^{30}$ | $R^{31}$ | A = |
|---|---|---|---|
| 147 | CH$_3$ | CH$_3$ | |

TABLE 10

| Compound No. | $R^{32}$ | $R^{33}$ | $R^{34}$ | A = |
|---|---|---|---|---|
| 148 | CH$_3$ | CH$_3$ | CH$_3$ | |
| 149 | CH$_3$ | CH$_3$ | C$_2$H$_5$ | |

TABLE 11

TABLE 11-continued

| Compound No. | $R^{35}$ | $R^{36}$ | $R^{37}$ | $R^{38}$ | A = |
|---|---|---|---|---|---|
| 150 | H | H | CH$_3$ | CH$_3$ | |
| 151 | H | H | OCH$_3$ | CH$_3$ | |
| 152 | H | CH$_3$ | OCH$_3$ | CH$_3$ | |

PREPARATION

The aromatic amine derivatives of the present invention may be prepared through a series of reactions as shown by the following formulae (1) and (2).

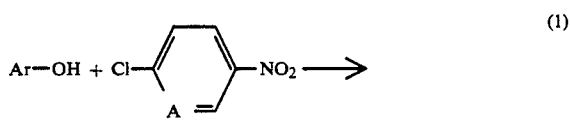

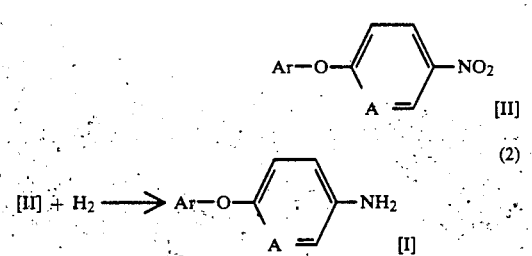

The reaction of formula (1) may be carried out by agitating the reagents in an aromatic hydrocarbon such as benzene, toluene, and xylene, an aprotic polar solvent such as N,N-dimethylformamide and 1-methyl-2-pyrrolidone, or a mixture thereof in the presence of a base such as NaOH, KOH, Na$_2$CO$_3$, K$_2$CO$_3$, NaH at a temperature of from 20° C. to 150° C. The reaction of formula (2) may proceed in a solvent inert to the reaction, for example, benzene, toluene, xylene, methanol, ethanol and ethyl acetate, in the presence of an ordinary reducing catalyst such as Raney nickel catalysts and palladium-carrying carbon under atmospheric pressure to a hydrogen pressure of 20 g/cm$^2$ at a temperature of from 20° C. to 100° C.

Among the compounds of general formula [II], those compounds represented by general formula [II-1]:

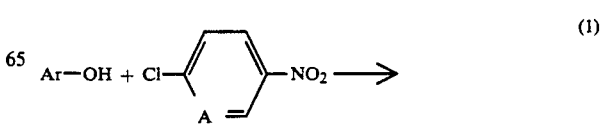

-continued

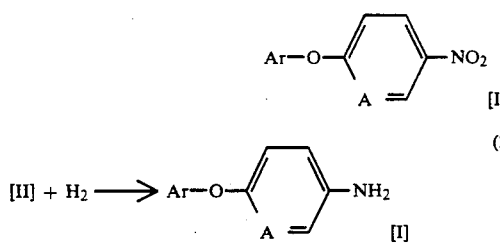

wherein $R^{11}$, $R^{12}$, $R^{13}$ and A are as defined above, $R^{16-1}$ is a lower alkoxy or hydroxyl radical can be produced not only by the reaction of formula (1), but also by a series of reactions as shown by formulae (3) and (4).

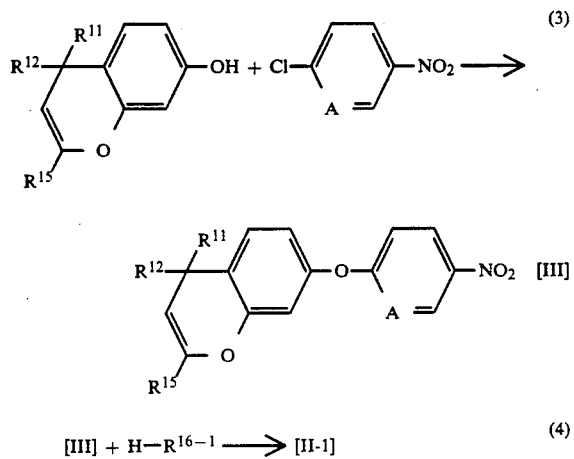

The reaction of formula (3) may proceed under the same conditions as described for the reaction of formula (1). The reaction of formula (4) may be carried out without solvent or in an inert solvent such as acetone, dioxane, benzene and toluene in the presence of an acid catalyst such as HCl, $H_2SO_4$ and Amberlist-15 by heating to a temperature of from 40° C. to 120° C.

Among the compounds of general formula [II], those compounds represented by general formula [II-2]:

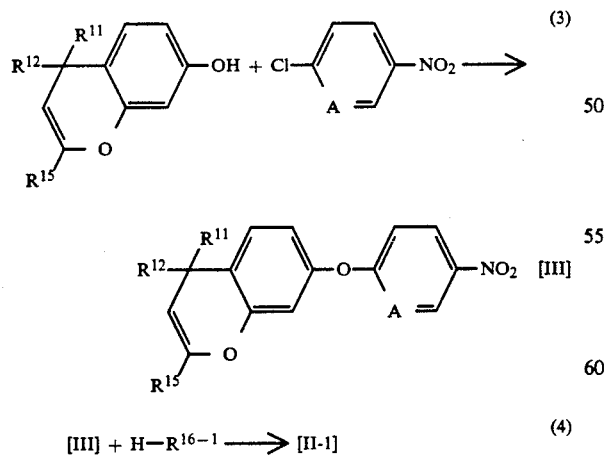

wherein $R^{11}$, $R^{12}$, and A are as defined above can be produced not only by the reaction of formula (1), but also by reaction as shown by formula (5).

$$[III] + :CCl_2 \rightarrow [II-2] \quad (5)$$

The reaction of formula (5) can be carried out by agitating a mixture of compound [III], chloroform, and NaOH or KOH without solvent or in an aqueous medium in the presence of a quaternary ammonium salt such as benzyltrimethyl ammonium chloride.

At the end of reaction, the end product can be recovered by a conventional method as shown in the following examples.

For typical ones of compounds Ar-OH used in the above preparation procedure, their typical synthesis is exemplified in Table 12 of Japanese Patent Application No. 61-177858 (WO 87/00840). Those compounds which are not exemplified in this Application may also be synthesized by a similar procedure.

EXAMPLES

Examples of the aromatic amine derivatives of the present invention are presented below by way of illustration and not by way of limitation.

REFERENCE 1

Synthesis of 2-(3-methyl-2,3-dihydro-6-benzofuryloxy)-5-nitropyridine

A 50-ml two-necked round-bottomed flask equipped with a dropping funnel was charged with 0.64 grams of sodium hydride and washed twice with n-hexane. To the flask were added dropwise 2.0 grams of 3-methyl-2,3-dihydro-6-benzofuranol and 10 ml of dimethylformamide at room temperature. After evolution of hydrogen ceased, 2.1 grams of 2-chloro-5-nitropyridine in 10 ml of dimethylformamide was added dropwise. The mixture was agitated for 3 hours at room temperature. After water was added to the reaction mixture, the product was extracted with ethyl acetate, washed with water, and then dried over anhydrous magnesium sulfate. The extracting solvent was distilled off to leave a residue, which was purified by chromatography through a silica gel column using a 4/1 n-hexane/ethyl acetate mixture, obtaining 3.0 grams of brown crystals (yield 83%).

Melting point 99.0°-99.5° C.

IR spectrum (KBr disk; $cm^{-1}$): 3120, 3020, 2950, 1605, 1585, 1515, 1420, 1340, 1240, 998

$^1$H-NMR spectrum ($CDCl_3$ solution; ppm)

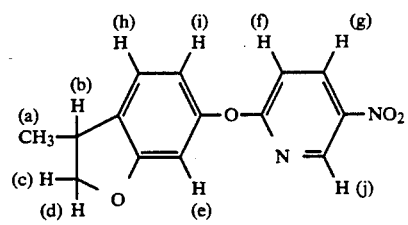

(a) 1.38(3H, d, J=9.0Hz)
(b) 3.60(1H, m)
(c) 4.18(1H, t, J=8.1Hz)
(d) 4.78(1H, t, J=8.1Hz)
(e) 6.63(1H, d, J=3.6Hz)
(f) 7.05(1H, d, J=9.0Hz)
(g) 7.50(1H, d, J=3.6 and 9.0Hz)
(h) 7.63(1H, d, J=7.2Hz)
(i) 7.68(1H, dd, J=3.6 and 7.2Hz)
(j) 8.10(1H, d, J=3.6Hz)

REFERENCE 2

Synthesis of 4-(3-methyl-2,3-dihydro-6-benzofuryloxy)-nitrobenzene

A 50-ml two-necked round-bottomed flask equipped with a Dean-Stark apparatus and a condenser was charged with 2.0 grams of 3-methyl-2,3-dihydro-6-benzofuranol, 2.1 grams of 4-chloronitrobenzene, 1.1 grams of 85% potassium hydroxide, 5.0 ml of toluene, and 5.0 ml of dimethylformamide. The mixture was agitated for 2½ hours at 140° C. while removing water formed. The reaction mixture was allowed to cool and then combined with water. The product was extracted with ethyl acetate, washed with water, and then dried over anhydrous magnesium sulfate. The extracting solvent was distilled off to leave a residue which was purified by chromatography through a silica gel column using a 4/1 n-hexane/ethyl acetate mixture, obtaining 3.1 grams of pale green crystals (yield 86%).

Melting point 90°–91° C.

IR spectrum (KBr disk; cm$^{-1}$): 3050, 2960, 1603, 1575, 1420, 1350, 1271, 1237, 1142, 997

$^1$H-NMR spectrum (CDCl$_3$ solution; ppm)

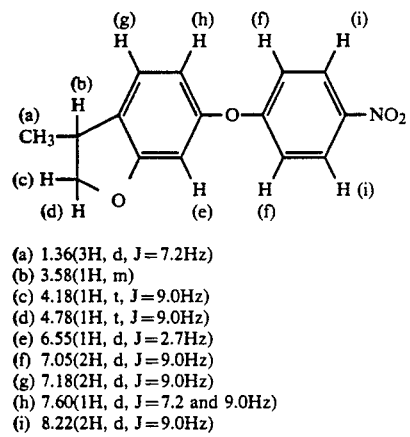

(a) 1.36(3H, d, J=7.2Hz)
(b) 3.58(1H, m)
(c) 4.18(1H, t, J=9.0Hz)
(d) 4.78(1H, t, J=9.0Hz)
(e) 6.55(1H, d, J=2.7Hz)
(f) 7.05(2H, d, J=9.0Hz)
(g) 7.18(2H, d, J=9.0Hz)
(h) 7.60(1H, d, J=7.2 and 9.0Hz)
(i) 8.22(2H, d, J=9.0Hz)

EXAMPLE 1

Compound No. 1: 2-(3-methyl-2,3-dihydro-6-benzofuryloxy)-5-aminopyridine

In 20 ml of ethyl acetate was dissolved 2.0 grams of 2-(3-methyl-2,3-dihydro-6-benzofuryloxy)-5-nitropyridine. The solution was catalytically reduced in the presence of 0.2 grams of 5% palladium-carrying carbon at room temperature. After absorption of hydrogen ceased, the catalyst was filtered off and the filtrate was concentrated. The concentrate was purified by chromatography through a silica gel column using ethyl acetate solvent, obtaining 1.7 grams of the end product in the form of colorless liquid (yield 97%).

Mass spectrum: m/z 242 (molecular ion peak)
IR spectrum (neat; cm$^{-1}$): 3400, 3050, 2950, 1602, 1357, 1271, 1235, 1130

$^1$H-NMR spectrum (CDCl$_3$ solution; ppm)

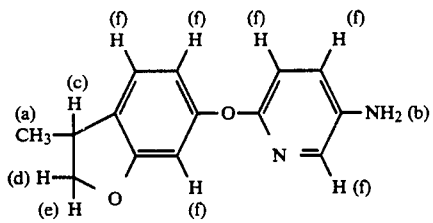

(a) 1.32(3H, d, J=7.2Hz)
(b) 3.28(2H, brs)
(c) 3.24~3.72(1H, m)
(d) 4.09(1H, t, J=7.2Hz)
(e) 4.72(1H, t, J=7.2Hz)
(f) 6.44~7.84(6H, m)

EXAMPLE 2

Compound No. 2: 4-(3-methyl-2,3-dihydro-6-benzofuryloxy)-aniline

The procedure of Example 1 was repeated except that the 2-(3-methyl-2,3-dihydro-6-benzofuryloxy)-5-nitropyridine was replaced by 4-(3-methyl-2,3-dihydro-6-benzofuryloxy)nitrobenzene. The reaction mixture was worked up in the same manner as in Example 1, obtaining the end product in the form of brown liquid (yield 98%).

Mass spectrum: m/z 241 (molecular ion peak)
IR spectrum (neat; cm$^{-1}$): 3350, 3050, 2970, 1601, 1357, 1270, 1236, 1132

$^1$H-NMR spectrum (CDCl$_3$ solution; ppm)

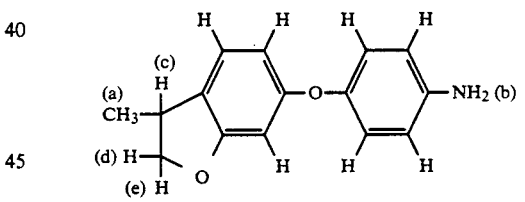

(a) 1.35(3H, d, J=7.2Hz)
(b) 3.37(2H, brs)
(c) 3.13~3.69(1H, m)
(d) 4.09(1H, t, J=7.2Hz)
(e) 4.70(1H, t, J=7.2Hz)
(f) 6.32~7.18(7H, m)

Compound Nos. 3 to 152 were synthesized by the same procedure as in Example 1. The results are summarized in Tabel 12. The yield was at least 95% for all the compounds.

TABLE 12

| Compound No. | As-produced | Spectral analysis |
|---|---|---|
| 3 | viscous liquid | NMR: 1.20(3H, d, J=8.1), 1.28(3H, s), 1.47(3H, s), 3.07(1H, q, J=8.1), 3.35(2H, brs), 6.24~8.00(6H, m). |
| 4 | viscous liquid | NMR: 1.19(3H, d, J=9.0), 1.45(3H, s), 3.10(1H, q, J=9.0), 3.38(2H, brs), 6.28~7.10(7H, m). |
| 5 | viscous liquid | NMR: 3.15(2H, t, J=7.2), 3.40(2H, brs), 4.60(2H, t, J=7.2), 6.20~7.40(7H, m). |
| 6 | viscous liquid | NMR: 0.96(3H, t, J=7.2), 1.70(2H, q, J=7.2), 3.30(1H, m), 3.42(2H, brs), 4.24(1H, t, J=9.0), 4.65(1H, t, J=9.0), 6.30~7.50(7H, m). |
| 7 | viscous liquid | IR: 3350($\nu_{NH}$), 3100, 2980, 1610, 1270, 1230. |
| 8 | viscous liquid | |

TABLE 12-continued

| Compound No. | As-produced | Spectral analysis |
|---|---|---|
| 9 | viscous liquid | NMR: 1.46(3H, d, J=7.2), 2.74(1H, dd, J=8.0, 15.0), 3.27(1H, dd, J=8.0, 15.0), 3.52(2H, brs), 4.94(1H, m), 6.28~7.42(7H, m). |
| 10 | viscous liquid | NMR: 1.04(3H, t, J=7.2), 1.76(2H, m), 2.78(1H, dd, J=8.0, 15.0), 3.22(1H, dd, J=8.0, 15.0), 3.55(2H, brs), 6.20~7.10(7H, m). |
| 11 | viscous liquid | NMR: 0.98(3H, d, J=7.2), 1.06(3H, d, J=7.2), 1.89(1H, m), 2.85(1H, dd, J=8.0, 15.0), 3.14(1H, dd, J=8.0, 15.0), 3.48(2H, brs), 4.54(1H, m), 6.35~7.20(7H, m). |
| 12 | viscous liquid | NMR: 0.93(3H, t, J=7.2), 1.00(3H, d, J=7.2), 1.61(3H, m), 2.70~3.30(2H, m), 3.42(2H, brs), 6.35~7.20(7H, m). |
| 13 | m.p. 86~87° C. | |
| 14 | viscous liquid | NMR: 0.95(3H, t, J=7.0), 1.40(3H, s), 1.74(2H, q, J=7.0), 2.95(2H, s), 3.42(2H, brs), 6.30~7.40(7H, m). |
| 15 | viscous liquid | NMR: 0.91(6H, t, J=7.0), 1.70(4H, q, J=7.0), 2.95(2H, s), 3.46(2H, brs), 6.30~7.20(7H, m). |
| 16 | viscous liquid | NMR: 0.90(3H, t, J=7.2), 1.14(3H, d, J=6.3), 1.17(3H, s), 1.70(2H, q, J=7.2), 3.08(1H, q, J=6.3), 3.30(2H, brs), 6.25~7.60(6H, m). |
| 17 | viscous liquid | NMR: 0.98(3H, t, J=7.2), 1.20(3H, d, J=6.3), 1.24(3H, s), 1.75(2H, q, J=7.2), 3.10(1H, q, J=6.3), 3.45(2H, brs), 6.30~7.20(7H, m). |
| 18 | viscous liquid | NMR: 0.99(3H, t, J=7.2), 1.22(3H, d, J=6.3), 1.24(3H, s), 1.78(2H, q, J=7.2), 3.18(1H, d, J=6.3), 3.52(2H, brs), 6.28~7.50(7H, m). |
| 19 | viscous liquid | IR: 3400, 3320($\mu_{NH}$). |
| 20 | viscous liquid | IR: 3410, 3310($\mu_{NH}$). |
| 21 | viscous liquid | NMR: 1.26(3H, t, J=7.2), 1.34(3H, s), 1.46(3H, s), 1.63(2H, m), 2.84(1H, t, J=9.0), 3.36(2H, brs), 6.18~7.16(7H, m). |
| 22 | viscous liquid | |
| 23 | viscous liquid | NMR: 1.49(3H, d, J=6.3), 2.80~3.40(2H, m), 3.55(2H, brs), 4.90(1H, m), 6.24~7.62(6H, m). |
| 24 | m.p. 101~102° C. | |
| 25 | viscous liquid | NMR: 1.29(3H, d, J=6.9), 3.52(3H, m), 4.12(1H, t, J=9.0), 4.71(1H, t, J=9.0), 6.20~7.15(7H, m). |
| 26 | viscous liquid | NMR: 0.94(3H, t, J=7.2), 1.70(2H, q, J=7.2), 3.44(3H, m), 4.21(1H, dd, J=7.2, 9.0), 4.63(1H, t, J=9.0), 6.15~7.50(7H, m). |
| 27 | viscous liquid | NMR: 0.96(3H, t, J=7.0), 1.24~1.78(4H, m), 3.10(1H, m), 3.42(2H, brs), 4.21(1H, dd, J=7.2, 9.0), 4.66(1H, t, J=9.0), 6.34~7.26(7H, m). |
| 28 | viscous liquid | |
| 29 | viscous liquid | |
| 30 | viscous liquid | NMR: 0.97(3H, t, J=7.2), 1.36~1.90(2H, m), 2.90~3.20(1H, m), 3.50(2H, brs), 3.53(3H, s), 5.26(3H, d, J=2.7), 6.52~7.36(7H, m). |
| 31 | viscous liquid | |
| 32 | m.p. 89.5~90.5° C. | |
| 33 | viscous liquid | |
| 35 | m.p. 94.5~95.5° C. | |
| 36 | viscous liquid | |
| 37 | viscous liquid | NMR: 1.27(3H, s), 1.29(3H, s), 3.30(2H, brs), 3.56(3H, s), 5.13(1H, s), 6.50~7.80(6H, m). |
| 38 | viscous liquid | NMR: 1.25(3H, s), 1.28(3H, s), 3.30(2H, brs), 3.56(3H, s), 5.11(1H, s), 6.48~7.00(7H, m). |
| 39 | viscous liquid | NMR: 1.24(3H, s), 1.28(3H, s), 3.34(3H, s), 3.60(2H, brs), 5.10(1H, s), 6.40~6.90(6H, m). |
| 40 | viscous liquid | |
| 41 | viscous liquid | |
| 42 | viscous liquid | NMR: 0.90(3H, d, J=6.4), 0.94(3H, d, J=6.4), 1.72~2.00(1H, m), 2.50~2.70(1H, m), 3.34(2H, brs), 5.32(3H, d, J=2.1), 6.40~7.20(7H, m). |
| 43 | viscous liquid | NMR: 0.96(3H, t, J=7.7), 1.23(3H, t, J=7.1), 1.40~1.84(2H, m), 3.01~3.16(1H, m), 3.52~4.00(4H, m), 5.38(1H, d, J=2.1), 6.41~7.18(7H, m). |
| 44 | viscous liquid | NMR: 0.88(3H, d, J=6.4), 0.92(3H, d, J=6.4), 1.24(3H, t, J=7.1), 1.80~2.12(1H, m), 3.02~3.12(1H, m), 3.52~4.06(4H, m), 5.44(1H, d, J=1.5), 6.40~7.18(4H, m). |
| 45 | viscous liquid | |
| 46 | viscous liquid | |
| 47 | viscous liquid | NMR: 1.30~2.16(8H, m), 3.13~3.36(1H, m), 3.52(2H, brs), 4.64~4.88(1H, m), 6.32~7.41(7H, m). |
| 48 | viscous liquid | IR: 3400($\nu_{NH}$), 3040, 2960, 1570, 1270, 1120. |
| 49 | viscous liquid | |
| 50 | viscous liquid | NMR: 3.48(2H, brs), 5.89(2H, s), 6.20~6.90(7H, m) |
| 51 | viscous liquid | NMR: 1.01(3H, t, J=7.2), 1.61(3H, s), 1.95(2H, q, J=7.2), 3.40(2H, brs), 6.20~7.10(7H, m). |
| 52 | viscous liquid | |
| 53 | viscous liquid | NMR: 1.68(6H, s), 3.45(2H, brs), 6.20~7.10(7H, m). |
| 54 | viscous liquid | NMR: 1.78(3H, s), 3.31(3H, s), 3.55(2H, brs), 6.30~7.00(7H, m). |
| 55 | viscous liquid | NMR: 1.21(3H, t, J=7.2), 1.80(3H, s), 3.32(2H, brs), 3.61(2H, q, J=7.2), 6.30~7.08(7H, m). |
| 56 | viscous liquid | NMR: 1.02(3H, t, J=7.2), 1.21(3H, t, J=7.2), 2.06(2H, q, J=7.2), 3.56(2H, q, J=7.2), 3.60(2H, brs), 6.30~7.00(7H, m). |
| 57 | viscous liquid | |
| 58 | viscous liquid | |
| 59 | viscous liquid | IR: 3400($\nu_{NH}$), 3060, 2970, 1603. |
| 60 | viscous liquid | |
| 61 | viscous liquid | IR: 3420($\nu_{NH}$), 3040, 2970, 1603, 1275. |
| 62 | viscous liquid | |
| 63 | viscous liquid | IR: 3400($\nu_{NH}$), 3060, 2955, 1605, 1275, 1238. |

TABLE 12-continued

| Compound No. | As-produced | Spectral analysis |
|---|---|---|
| 64 | m.p. 109~110° C. | |
| 65 | viscous liquid | NMR: 1.38(3H, d, J=7.2), 1.60~2.00(2H, m), 2.64~2.94(2H, m), 3.37(2H, m), 6.40~7.80(6H, m). |
| 66 | viscous liquid | NMR: 1.38(3H, d, J=9.0), 1.80(2H, m), 2.72(2H, m), 2.64(2H, brs), 4.16(1H, m), 6.40~7.80(6H, m). |
| 67 | m.p. 115.5~116.5° C. | |
| 68 | m.p. 93~94° C. | NMR: 1.30(6H, s), 1.76(2H, t, J=7.2), 2.72(2H, t, J=7.2), 3.38(2H, brs), 6.40~7.80(6H, m). |
| 69 | viscous liquid | NMR: 1.30(6H, s), 1.77(2H, t, J=7.2), 2.72(2H, t, J=7.2), 3.44(2H, brs), 6.20~7.18(7H, m). |
| 70 | viscous liquid | NMR: 1.32(6H, s), 1.78(2H, t, J=7.2), 2.72(2H, t, J=7.2), 3.64(2H, brs), 6.20~7.10(6H, m). |
| 71 | viscous liquid | IR: 3420($\nu_{NH}$), 3040, 2970, 1605, 1535, 1370. |
| 72 | viscous liquid | |
| 73 | viscous liquid | NMR: 1.29(3H, s), 1.32(3H, d, J=7.2), 1.62(1H, s), 1.68(1H, s), 3.28(2H, brs), 4.16(1H, q, J=7.2), 6.40~7.80(6H, m). |
| 74 | viscous liquid | |
| 75 | viscous liquid | IR: 3380($\mu_{NH}$), 3180, 3040, 2960, 1605, 1275. |
| 76 | viscous liquid | IR: 3410($\mu_{NH}$), 3060, 2970, 1610, 1270, 1235, 1140. |
| 77 | viscous liquid | NMR: 1.32(3H, s), 1.41(3H, s), 1.99(1H, d, J=7.2), 2.03(1H, d, J=7.2), 3.44(3H, s), 3.50(2H, brs), 4.38(1H, t, J=7.2), 6.20~7.40(7H, m). |
| 78 | m.p. 104.5~105.5° C. | |
| 79 | viscous liquid | NMR: 1.26(3H, s), 1.41(3H, s), 1.49(3H, s), 1.81(1H, d, J=14.0), 1.95(1H, d, J=14.0), 2.65(2H, brs), 3.23(3H, s), 6.40~7.30(7H, m). |
| 80 | viscous liquid | NMR: 1.25(3H, s), 1.41(3H, s), 1.48(3H, s), 1.80(1H, d, J=14.4), 2.02(1H, d, J=14.4), 3.21(3H, s), 3.64(2H, brs), 6.20~7.32(7H, m). |
| 81 | viscous liquid | IR: 3410($\nu_{NH}$), 3330($\nu_{NH}$), 1610, 1524, 1470, 1350, 1265, 1230. |
| 82 | viscous liquid | |
| 83 | viscous liquid | NMR: 1.00(3H, t, J=7.2), 1.26(3H, s), 1.44(3H, s), 1.50(3H, s), 1.88(1H, d, J=14.0), 1.95(1H, d, J=14.0), 3.35(2H, brs), 3.55(2H, q, J=7.2), 6.32~7.30(7H, m). |
| 84 | viscous liquid | NMR: 0.72(3H, t, J=7.2), 1.20~1.60(2H, m), 1.28(3H, s), 1.46(3H, s), 1.54(3H, s), 1.84(1H, d, J=13.5), 2.05(1H, d, J=13.5), 3.47(4H, m), 6.20~7.20(7H, m). |
| 85 | viscous liquid | NMR: 0.84, 1.11(total 6H, d, J=7.2), 1.25(3H, s), 1.45(3H, s), 1.51(3H, s), 1.74(1H, d, J=13.5), 1.99(1H, d, J=13.5), 3.56(2H, brs), 4.12(1H, m), 6.30~7.26(7H, m). |
| 86 | viscous liquid | NMR: 1.82~2.20(2H, m), 3.43(3H, s), 3.48(2H, brs), 4.10~4.36(3H, m), 6.30~7.35(7H, m). |
| 87 | viscous liquid | NMR: 1.00(3H, t, J=7.2), 1.40~2.16(4H, m), 2.50~3.00(2H, m), 3.50(2H, brs), 3.70~4.04(1H, m), 6.20~7.33(7H, m). |
| 88 | viscous liquid | |
| 89 | viscous liquid | NMR: 1.90(2H, m), 2.56(2H, m), 3.40(3H, s), 3.52(2H, brs), 5.01(1H, t, J=1.8), 6.18~7.31(7H, m). |
| 90 | viscous liquid | |
| 91 | viscous liquid | NMR: 1.00(3H, t, J=7.2), 1.80(4H, m), 2.60(1H, m), 3.48(2H, brs), 4.16(2H, t, J=5.4), 6.10~7.15(7H, m). |
| 92 | viscous liquid | NMR: 0.97(3H, d, J=7.2), 1.18(3H, d, J=7.2), 2.00~2.10(1H, m), 2.72~3.04(1H, m), 3.48(2H, brs), 3.78~4.20(2H, m), 6.30~7.10(7H, m). |
| 93 | viscous liquid | |
| 94 | viscous liquid | NMR: 1.30, 1.35(total 3H, d, J=7.2), 1.60~2.28(2H, m), 2.94(1H, m), 3.47, 3.51(total 3H, s), 3.49(2H, brs), 6.30~7.42(7H, m). |
| 95 | viscous liquid | NMR: 1.00~1.50(6H, m), 1.60~2.28(2H, m), 3.08(1H, m), 3.24~4.08(4H, m), 5.20(1H, dd, J=3.6, 7.2), 6.32~7.46(7H, m). |
| 96 | viscous liquid | NMR: 1.40(3H, d, J=7.2), 1.62~2.44(2H, m), 3.44(3H, s), 3.54(2H, brs), 4.20(1H, m), 4.56(1H, dd, J=6.3, 10.8), 6.21~7.32(7H, m). |
| 97 | viscous liquid | |
| 98 | viscous liquid | NMR: 0.96(3H, d, J=7.2), 1.26(3H, d, J=7.2), 2.00~3.08(3H, m), 3.48(2H, m), 4.08~4.18(1H, m), 6.33~7.20(7H, m). |
| 99 | viscous liquid | NMR: 0.82~1.12(6H, m), 1.20~1.81(3H, m), 2.20~2.80(2H, m), 3.48(2H, brs), 4.10(1H, m), 6.24~7.26(7H, m). |
| 100 | viscous liquid | |
| 101 | viscous liquid | IR: 3420($\nu_{NH}$), 3070, 2940, 1570, 1275, 1238. |
| 102 | viscous liquid | IR: 3420($\nu_{NH}$), 3050, 2955, 1610, 1570, 1575, 1240. |
| 103 | viscous liquid | |
| 104 | m.p. 85~86° C. | NMR: 0.89(6H, t, J=7.2), 1.25~1.67(6H, m), 1.78(2H, t, J=7.2), 2.68(2H, t, J=7.2), 3.48(2H, brs), 6.32~7.22(7H, m). |
| 105 | viscous liquid | |
| 106 | viscous liquid | NMR: 1.55(3H, s), 1.64~2.24(2H, m), 2.36~3.04(2H, m), 3.28(2H, brs), 3.30(3H, s), 6.36~7.10(7H, m). |
| 107 | viscous liquid | NMR: 1.04(3H, t, J=7.2), 1.58(3H, s), 1.70~2.28(2H, m), 2.60~3.24(2H, m), 3.48(2H, brs), 3.62(2H, q, J=7.2), 6.36~7.40(7H, m). |
| 108 | viscous liquid | NMR: 0.85(3H, t, J=7.2), 1.14(3H, t, J=7.2), 1.54(3H, s), 1.66~2.24(2H, m), 2.40~2.80(2H, m), 3.49(2H, brs), 4.22(1H, m), 6.26~7.38(7H, m). |
| 109 | viscous liquid | NMR: 0.95(3H, t, J=7.2), 1.50~2.20(4H, m), 2.40~3.00(2H, m), 3.24(3H, s), 3.38(2H, brs), 6.36~7.08(7H, m). |
| 110 | viscous liquid | |
| 111 | viscous liquid | |
| 112 | viscous liquid | NMR: 1.08(3H, d, J=7.2), 1.40(3H, d, J=7.2), 1.60~2.00(1H, m), 3.31(3H, s), 3.51(2H, brs), 3.80~4.36(2H, m), 6.20~7.40(7H, m). |
| 113 | viscous liquid | NMR: 0.99(3H, d, J=7.2), 1.14(3H, s), 1.35(3H, s), 1.62~2.10(1H, m), 2.30~2.88(2H, m), 3.47(2H, brs), 6.30~7.12(7H, m). |

TABLE 12-continued

| Compound No. | As-produced | Spectral analysis |
|---|---|---|
| 114 | viscous liquid | NMR: 1.08(3H, d, J=7.2), 1.49(3H, s), 1.98(1H, m), 2.46~2.76(2H, m), 3.23(3H, s), 3.42(2H, brs), 6.20~7.12(7H, m). |
| 115 | viscous liquid | NMR: 0.94(3H, t, J=7.2), 1.25 and 1.36(total 3H, s), 1.50~1.76(2H, m), 1.81~2.12(2H, m), 3.44 and 3.46(total 3H, s), 3.54(2H, brs), 4.41(1H, brs), 6.24~7.30(7H, m). |
| 116 | viscous liquid | |
| 117 | viscous liquid | NMR: 0.89(6H, t, J=7.2), 1.50~2.10(6H, m), 3.44(3H, s), 3.50(2H, brs), 4.37(1H, t, J=6.3), 6.20~7.40(7H, m). |
| 118 | viscous liquid | NMR: 0.90(6H, t, J=7.2), 1.10~2.20(8H, m), 3.46(3H, s), 3.52(2H, brs), 4.38(1H, t, J=7.2), 6.30~7.40(7H, m). |
| 119 | viscous liquid | |
| 120 | viscous liquid | NMR: 1.04(3H, t, J=7.2), 1.52~2.14(4H, m), 3.42(3H, brs), 3.92~4.40(5H, m), 6.20~7.20(7H, m). |
| 121 | viscous liquid | NMR: 1.00(6H, d, J=6.3), 1.85~1.94(3H, m), 3.47(2H, brs), 4.04(1H, m), 4.15(4H, m), 6.30~7.32(7H, m). |
| 122 | viscous liquid | NMR: 0.97(3H, d, J=7.0), 1.38(3H, d, J=7.0), 2.12(1H, m), 3.50(2H, brs), 4.09~4.35(5H, m), 6.33~7.18(7H, m). |
| 123 | viscous liquid | NMR: 1.42(6H, s), 2.13(2H, s), 3.50(2H, brs), 4.00~4.30(4H, m), 6.24~7.14(7H, m). |
| 124 | viscous liquid | NMR: 0.92(3H, t, J=7.0), 1.34(3H, s), 1.70(2H, q, J=7.2), 2.01(1H, d, J=14.4), 2.20(1H, d, J=14.4), 3.20(2H, brs), 4.00~4.30(4H, m), 6.30~7.44(7H, m). |
| 125 | viscoud liquid | |
| 126 | viscous liquid | NMR: 0.87(6H, t, J=7.2), 1.68(4H, q, J=7.2), 2.10(2H, s), 3.42(2H, brs), 4.00~4.30(4H, m), 6.22~7.20(7H, m). |
| 127 | viscous liquid | NMR: 0.88(6H, t, J=7.2), 1.10~1.50(2H, m), 1.69(4H, q, J=7.2), 2.09(2H, s), 3.49(2H, brs), 3.90~4.30(4H, m), 6.18~7.10(7H, m). |
| 128 | viscous liquid | NMR: 1.36(3H, s), 1.62(3H, s), 1.68(1H, s), 1.80(3H, s), 3.54(2H, brs), 6.20~7.18(7H, m). |
| 129 | viscous liquid | NMR: 1.80~2.24(6H, m), 3.06(1H, m), 3.53(3H, s), 3.55(2H, brs), 6.32~7.22(7H, m). |
| 130 | viscous liquid | NMR: 1.40~1.92(6H, m), 2.00~2.30(2H, m), 3.18(1H, m), 3.50(2H, brs), 3.76(3H, s), 6.18~7.32(7H, m). |
| 131 | m.p. 140.0~141.0 | IR: 3385, 3320($\nu_{NH}$), 3040($\nu_{NH}$), 1610, 1578, 1498, 1208, 1132, 1162, 990. NMR: 1.31(3H, s), 1.47(3H, s), 1.60(3H, s), 1.82(1H, d, J=13.5), 2.04(1H, d, J=13.5), 3.12(2H, brs), 6.35(1H, d, J=2.7), 6.55(1H, dd, J=2.7, 9.0), 6.65(2H, d, J=9.0), 6.89(2H, d, J=9.0), 7.20(1H, d, J=9.0). |
| 132 | viscous liquid | NMR: 1.40(3H, d, J=7.2), 1.80(2H, m), 2.74(2H, m), 3.48(2H, brs), 4.12(1H, m), 6.60~7.84(6H, m). |
| 133 | viscous liquid | NMR: 1.38(2H, d, J=7.2), 1.80(2H, m), 2.70(2H, m), 3.52(2H, brs), 4.11(1H, m), 6.52~6.96(7H, m). |
| 134 | viscous liquid | NMR: 1.33(6H, s), 1.78(2H, t, J=7.2), 2.75(2H, t, J=7.2), 3.25(2H, brs), 6.60~7.80(6H, m). |
| 135 | viscous liquid | |
| 136 | viscous liquid | |
| 137 | viscous liquid | NMR: 1.55(3H, s), 1.66~2.21(2H, m), 2.32~3.10(2H, m), 3.22(2H, brs), 3.30(3H, s), 6.50~7.00(7H, m). |
| 138 | viscous liquid | NMR: 1.35(6H, d, J=6.9), 2.98~3.10(1H, m), 3.48(2H, brs), 6.36(1H, s), 6.30~7.32(7H, m). |
| 139 | viscous liquid | NMR: 0.98(3H, d, J=6.9), 1.02(3H, d, J=6.9), 1.90~2.28(1H, m), 2.64(2H, dd, J=2.7, 6.7), 3.47(2H, brs), 6.32(1H, s), 6.34~7.18(7H, m). |
| 140 | viscous liquid | NMR: 1.30(3H, t, J=7.7), 2.64(2H, q, J=7.7), 6.32~7.34(8H, m). |
| 141 | viscous liquid | NMR: 0.80~1.84(5H, m), 1.56(2H, t, J=7.7), 3.50(2H, brs), 6.20~7.40(8H, m). |
| 142 | viscous liquid | NMR: 1.30(6H, d, J=6.7), 2.90~3.14(1H, m), 3.47(2H, brs), 6.20~7.35(8H, m). |
| 143 | viscous liquid | NMR: 1.42(3H, d, J=6.3), 2.84(1H, dd, J=7.2, 14.4), 2.96(1H, dd, J=7.2, 14.4), 3.56(2H, brs), 4.92(1H, m), 6.20~7.60(6H, m). |
| 144 | viscous liquid | NMR: 1.48(3H, d, J=6.4), 2.88(1H, dd, J=7.7, 15.4), 3.38(1H, dd, J=7.7, 15.4), 3.52(2H, brs), 5.00(1H, m), 6.38~7.32(8H, m). |
| 146 | viscous liquid | NMR: 1.26(6H, s), 1.80(2H, t, J=7.1), 2.82(2H, t, J=7.1), 3.52(2H, brs), 6.33~7.10(7H, m). |
| 147 | viscous liquid | |
| 148 | viscous liquid | NMR: 1.19(3H, d, J=7.2), 1.37(3H, s), 1.40(3H, s), 2.24(3H, s), 3.10(1H, q, J=7.2), 3.48(2H, brs), 6.20~7.20(6H, m). |
| 149 | viscous liquid | NMR: 0.92(3H, t, J=7.2), 1.18(3H, d, J=6.3), 1.30(3H, s), 1.68(2H, q, J=7.2), 2.20(3H, s), 3.12(1H, q, J=6.3), 3.52(2H, brs), 6.30~7.22(6H, m). |
| 150 | viscous liquid | NMR: 1.30(3H, s), 1.82(2H, t, J=6.7), 2.16(3H, s), 2.60(2H, t, J=6.7), 3.52(2H, brs), 6.20~7.12(6H, m). |
| 151 | viscous liquid | |
| 152 | viscous liquid | NMR: 1.16(3H, d, J=7.2), 1.52(3H, s), 1.80~2.12(1H, m), 2.22(3H, s), 2.44(2H, d, J=9.0), 3.24(3H, s), 3.48(2H, brs), 6.24~7.42(6H, m). |

The aromatic amine derivatives of the present invention are useful as intermediates for herbicides.

More particularly, compounds of general formula [IV]:

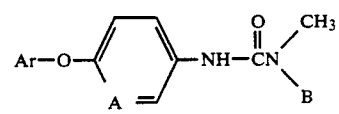

wherein Ar and A are as defined above, and B is a hydrogen atom, a methyl or methoxy radical can be produced from the aromatic amine derivatives of the present invention by the method described in Japanese Patent Application No. 61-177858 (WO 87/00840) which is assigned to the same assignee as the present invention and whose disclosure is incorporated herein by reference. The compounds of formula [IV] are effective as herbicides as described in Japanese Patent Application No. 61-177858 (WO 87/00840). The specification of the Application reports the measured physical properties of the compounds, to which the measured physical properties of the aromatic amine derivatives of the present invention conform.

We claim:

1. The aromatic amine compound of the formula:

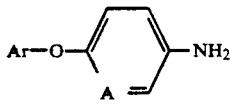

wherein Ar is a radical selected from the group consisting of

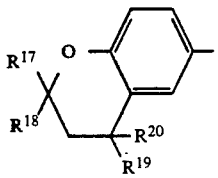

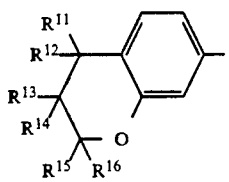

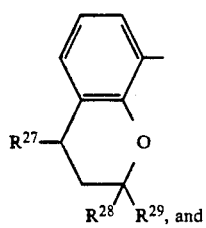

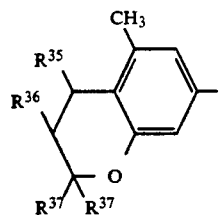

wherein $R^{11}$ to $R^{15}$, $R^{17}$ to $R^{20}$, $R^{27}$–$R^{29}$ and $R^{35}$ to $R^{38}$ may be the same of different and are independently selected from the group consisting of hydrogen, lower alkyl radicals, and lower alkoxy radicals, $R^{16}$ is selected from the group consisting of hydrogen, lower alkyl radicals, lower alkoxy radicals and hydroxyl, with the provisos that at least one of $R^{11}$ to $R^{16}$ is a lower alkoxy radical or hydroxyl radical; $R^{11}$ and $R^{15}$, or $R^{15}$ and $R^{16}$ may, taken together, represent an alkylene chain, which may be substituted with a lower alkyl radical, to form a 5- or 6-membered ring with the carbon atoms to which they are attached, $R^{11}$ and $R^{12}$ may, taken together, represent an ethylene dioxyl radical, or $R^{14}$ or $R^{15}$ may, taken together, represent a dichloromethylene radical; at least one of $R^{17}$ to $R^{20}$ is a lower alkoxy radical; at least one of $R^{27}$ to $R^{29}$ is a lower alkoxy radical; and at least one of $R^{35}$ to $R^{38}$ is a lower alkoxy radical; and

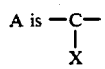

wherein X is selected from the group consisting of a hydrogen atom, a chlorine atom, and a trifluoromethyl radical.

2. An aromatic amine as set forth in claim 1, wherein Ar is a group of the formula

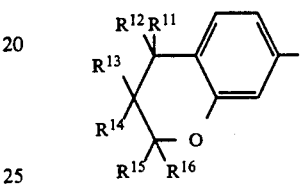

wherein $R^{11}$ to $R^{16}$ are as defined.

3. An aromatic amine according to claim 2, wherein X is a hydrogen atom.

4. An aromatic amine according to claim 2, wherein X is a chlorine atom.

5. An aromatic amine according to claim 2, wherein X is a trifluoromethyl radical.

6. An aromatic amine as set forth in claim 1 wherein Ar is a group of the formula

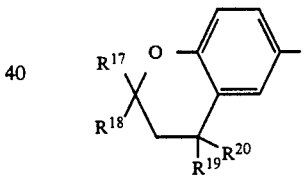

wherein $R^{17}$–$R^{20}$ are as defined.

7. An aromatic amine according to claim 6, wherein X is a hydrogen atom.

8. An aromatic amine according to claim 6, wherein X is a chlorine atom.

9. An aromatic amine according to claim 6, wherein X is a trifluoromethyl radical.

10. An aromatic amine as set forth in claim 1, wherein Ar is a group of the formula

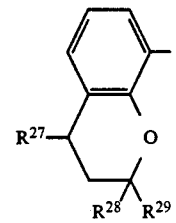

wherein $R^{27}$–$R^{29}$ are as defined.

11. An aromatic amine according to claim 10, wherein X is a hydrogen atom.

12. An aromatic amine according to claim 10, wherein X is a chlorine atom.

13. An aromatic amine according to claim 10, wherein X is a trifluoromethyl radical.

14. An aromatic amine as set forth in claim 1, wherein Ar is a group of the formula

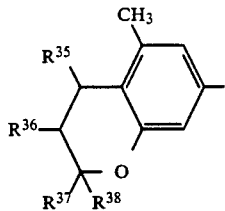

wherein $R^{35}$-$R^{38}$ are as defined.

15. An aromatic amine according to claim 14, wherein x is a hydrogen atom.

16. An aromatic amine according to claim 14, wherein x is a chlorine atom.

17. An aromatic amine according to claim 14, wherein X is a trifluoromethyl radical.

18. An aromatic amine as set forth in claim 3, wherein $R^{11}$ is hydrogen, methyl, ethyl or methoxy, $R^{12}$ is hydrogen or methyl or $R^{11}$ and $R^{12}$ together represent the group —O(CH$_2$)$_2$O—, $R^{13}$ is hydrogen or methyl, $R^{14}$ is hydrogen, $R^{15}$ is hydrogen or methyl, ethyl, i-propyl, methoxy or ethoxy or $R^{14}$ and $R^{15}$ together represent dichloromethylene, $R^{16}$ is hydrogen or methyl, ethyl, n-propyl, i-propyl, methoxy, ethoxy, n-propoxy or i-propoxy or $R^{15}$ and $R^{16}$ together represent pentamethylene.

19. An aromatic amine as set forth in claim 4, wherein $R^{11}$ is hydrogen, methyl, ethyl or methoxy, $R^{12}$ is hydrogen or methyl or $R^{11}$ and $R^{12}$ together represent the group —O(CH$_2$)$_2$O—, $R^{13}$ is hydrogen or methyl, $R^{14}$ is hydrogen, $R^{15}$ is hydrogen or methyl, ethyl, i-propyl, methoxy or ethoxy or $R^{14}$ and $R^{15}$ together represent dichloromethylene, $R^{16}$ is hydrogen or methyl, ethyl, n-propyl, i-propyl, methoxy, ethoxy, n-propoxy or i-propoxy or $R^{15}$ and $R^{16}$ together represent pentamethylene.

20. An aromatic amine as set forth in claim 5, wherein $R^{11}$ is hydrogen, methyl, ethyl or methoxy, $R^{12}$ is hydrogen or methyl or $R^{11}$ and $R^{12}$ together represent the group —O(CH$_2$)$_2$O—, $R^{13}$ is hydrogen or methyl, $R^{14}$ is hydrogen, $R^{15}$ is hydrogen or methyl, ethyl, i-propyl, methoxy or ethoxy or $R^{14}$ and $R^{15}$ together represent dichloromethylene, $R^{16}$ is hydrogen or methyl, ethyl, n-propyl, i-propyl, methoxy, ethoxy, n-propoxy or i-propoxy or $R^{15}$ and $R^{16}$ together represent pentamethylene.

21. An amine compound as set forth in claim 7, wherein $R^{17}$ is hydrogen or methyl, $R^{18}$ is methoxy, $R^{19}$ is hydrogen or methyl and $R^{20}$ is hydrogen or methyl.

22. An amine compound as set forth in claim 8, wherein $R^{17}$ is hydrogen or methyl, $R^{18}$ is methoxy, $R^{19}$ is hydrogen or methyl and $R^{20}$ is hydrogen or methyl.

23. An amine compound as set forth in claim 9, wherein $R^{17}$ is hydrogen or methyl, $R^{18}$ is methoxy, $R^{19}$ is hydrogen or methyl and $R^{20}$ is hydrogen or methyl.

24. An aromatic amine as set forth in claim 15, wherein $R^{35}$ is hydrogen, $R^{36}$ is hydrogen or methyl, $R^{37}$ is methoxy and $R^{38}$ is methyl.

25. An aromatic amine as set forth in claim 16, wherein $R^{35}$ is hydrogen, $R^{36}$ is hydrogen or methyl, $R^{37}$ is methoxy and $R^{38}$ is methyl.

26. An aromatic amine as set forth in claim 17, wherein $R^{35}$ is hydrogen, $R^{36}$ is hydrogen or methyl, $R^{37}$ is methoxy and $R^{38}$ is methyl.

* * * * *